US011256973B2

(12) United States Patent
Madi et al.

(10) Patent No.: US 11,256,973 B2
(45) Date of Patent: Feb. 22, 2022

(54) NEURAL NETWORK WITH EMBEDDED FILTER LAYER

(71) Applicant: Nuance Communications, Inc., Burlington, MA (US)

(72) Inventors: Nasr Madi, Montreal (CA); Neil D. Barrett, Longueuil (CA)

(73) Assignee: Nuance Communications, Inc., Burlington, MA (US)

( * ) Notice: Subject to any disclaimer, the term of this patent is extended or adjusted under 35 U.S.C. 154(b) by 857 days.

(21) Appl. No.: 15/888,812

(22) Filed: Feb. 5, 2018

(65) Prior Publication Data

US 2019/0244076 A1    Aug. 8, 2019

(51) Int. Cl.
*G06N 3/04* (2006.01)
*G06N 3/08* (2006.01)
*G16H 50/20* (2018.01)

(52) U.S. Cl.
CPC .............. *G06N 3/04* (2013.01); *G06N 3/08* (2013.01); *G16H 50/20* (2018.01)

(58) Field of Classification Search
CPC ............. G06N 3/04; G06N 3/08; G16H 50/20
See application file for complete search history.

(56) References Cited

U.S. PATENT DOCUMENTS

| 2015/0161995 | A1* | 6/2015 | Sainath | G10L 15/063 704/232 |
| 2017/0046614 | A1* | 2/2017 | Golovashkin | G06N 3/082 |
| 2018/0285734 | A1* | 10/2018 | Chen | G06N 3/08 |

OTHER PUBLICATIONS

Ng, Andrew. "Sparse Autoencoder", pp. 12-16 Verified online as of 2015 by web.archive.org: https://web.archive.org/web/20150219073254/https://web.stanford.edu/class/cs294a/sparseAutoencoder_2011new.pdf (Year: 2015).*
Wen, Wei, et al. "Learning structured sparsity in deep neural networks." arXiv preprint arXiv: 1608.03665 (2016). (Year: 2016).*
Luo et al. "Thinet: A filter level pruning method for deep neural network compression." Proceedings of the IEEE international conference on computer vision. 2017. (Year: 2017).*
Oneto, Luca, Sandro Ridella, and Davide Anguita. "Tikhonov, Ivanov and Morozov regularization for support vector machine learning." Machine Learning 103.1 (2016): 103-136. (Year: 2016).*

(Continued)

*Primary Examiner* — Abdullah Al Kawsar
*Assistant Examiner* — Asher Jablon
(74) *Attorney, Agent, or Firm* — Hamilton, Brook, Smith & Reynolds, P.C.

(57) ABSTRACT

A neural network embodiment comprises an input layer, an output layer and a filter layer. Each unit of the filter layer receives a filter layer input from a single preceding unit via a respective filter layer input connection. Each filter layer input connection is coupled to a different single preceding unit. The filter layer incentivizes the neural network to learn to produce a target output from the output layer for a given input to the input layer while simultaneously learning weights for each filter layer input connection. The weights learned cause the filter layer to reduce a number of filter layer units that pass respective filter layer inputs as non-zero values. When applied as an initial internal layer between an input layer and an output layer, the filter layer incentivizes the neural network to learn which neural network input features to discard to produce the target output.

18 Claims, 9 Drawing Sheets

(56) References Cited

OTHER PUBLICATIONS

Li et al. "Deep Feature Selection: Theory and Application to Identify Enhancers and Promoters". Journal of Computational Biology, vol. 23, No. 5. May 2016. 322-336. (Year: 2016).*
Scardapane, Simone, et al. "Group sparse regularization for deep neural networks." Neurocomputing 241 (2017): 81-89. (Year: 2017).*
"Overfitting," https://en.wikipedia.org/wiki/Overfitting, downloaded from the internet Jan. 24, 2018, pp. 1-5.

* cited by examiner

NEURAL NETWORK WITH EMBEDDED FILTER LAYER

BACKGROUND

In machine learning, feature selection is any process of selecting a subset of features (input parameters) to use within a model. Feature selection has many advantages, including simplifying the model and reducing overfitting to enhance generalization. As many real-world machine learning problems involve a large number of features where only a subset of which is relevant, feature selection is often needed and is often used. In particular, feature selection is important in healthcare-related artificial intelligence (AI) applications where there is frequently little data and the applications require complex models.

SUMMARY

According to an example embodiment, a neural network may comprise an input layer, an output layer, and a filter layer. Each unit of the filter layer may be configured to receive a filter layer input from a single preceding unit via a respective filter layer input connection. Each filter layer input connection may be coupled to a different single preceding unit. The filter layer is configured to incentivize the neural network to learn to produce a target output from the output layer for a given input to the input layer while simultaneously learning weights for each filter layer input connection. The weights learned cause the filter layer to reduce a number of filter layer units that pass respective filter layer inputs as non-zero values. A weight that is applied to a filter layer input connection may be referred to interchangeably herein as a filter weight.

At least one of the weights learned has a negative value. A mean of the weights learned may be a given average value and each unit of the filter layer may be configured to apply a rectified linear unit (ReLU) activation function to force all outputs from the unit to zero in an event a weight learned for its respective filter layer input connection is negative.

The filter layer may be further configured to incentivize the neural network to minimize a regularized loss function that is expressed on the filter layer that combines an underlying loss function with a penalty function imposed on the weights learned.

The regularized loss function may be deemed to be minimized in an event (i) a difference between an actual output from the output layer and the target output is less than or equal to a given acceptable difference and (ii) the weights learned have an average value that matches a given value causing the penalty function to achieve its minimum. The given acceptable difference may be deemed acceptable based on a pre-determined tolerance, such as +/−1%, +/−10%, or another suitable tolerance for a given application. With respect to the average value, a non-positive (i.e., zero or negative) average value, such as zero or a negative value, provides stricter filtering, whereas a positive average value provides less filtering and, possibly, no filtering.

The filter layer may be a feature selection layer that is an initial hidden layer of the neural network, and each filter layer input may be an input feature to the neural network.

The filter layer may be a last hidden layer of the neural network.

The filter layer may have input connections and output connections to respective units of internal layers that are neither input layers nor output layers.

Each single preceding unit may be located in a common preceding layer that precedes the filter layer in the neural network.

At least two units of the filter layer may be configured to receive respective filter layer inputs from corresponding single preceding units located in different preceding layers that precede the filter layer in the neural network.

The filter layer may be a first filter layer, and the neural network may further comprise at least one other filter layer.

The neural network may be a densely connected neural network that includes the filter layer integrated therein.

According to another example embodiment, a method for filtering in a neural network may comprise incentivizing the neural network, via a filter layer integrated within the neural network, to learn to produce a target output from an output layer for a given input to an input layer while simultaneously learning weights for each filter layer input connection, each unit of the filter layer configured to receive a filter layer input from a single preceding unit via a respective filter layer input connection. Each filter layer input connection may be coupled to a different single preceding unit. The method may comprise learning the weights for each filter layer input connection to the filter layer, the weights learned may cause the filter layer to reduce a number of filter layer units of the filter layer that pass respective filter layer inputs as non-zero values.

The method may further comprise applying a rectified linear unit (ReLU) activation function by each unit to force all outputs from the unit to zero in an event a weight learned for its respective filter layer input connection is negative. At least one of the weights learned may have a negative value, and a mean of the weights learned may be a given average value.

The method may further comprise expressing a regularized loss function on the filter layer that combines an underlying loss function with a penalty function imposed on the weights learned. Incentivizing the neural network may include incentivizing the neural network to minimize the regularized loss function.

The method may further comprise deeming the regularized loss function to be minimized in an event (i) a difference between an actual output from the output layer and the target output is less than or equal to a given acceptable difference and (ii) the weights learned have an average value that matches a given value causing the penalty function to achieve its minimum.

The filter layer may be a feature selection layer that is an initial hidden layer of the neural network, and each filter layer input may be an input feature to the neural network.

The filter layer may be a last hidden layer of the neural network, or the filter layer may have input connections and output connections to respective units of internal layers that are neither input layers nor output layers.

The method may further comprise including each single preceding unit in a common preceding layer that precedes the filter layer in the neural network or configuring at least two units of the filter layer to receive respective filter layer inputs from corresponding single preceding units included in different preceding layers that precede the filter layer in the neural network.

The filter layer may be a first filter layer, and the method may further comprise including at least one other filter layer in the neural network.

The neural network may be a densely connected neural network that includes the filter layer integrated therein.

It should be understood that example embodiments disclosed herein can be implemented in the form of a method, apparatus, system, or computer readable medium with program codes embodied thereon.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Feature selection methods may improve accuracy of a predictive model by choosing features that yield as good or better accuracy whilst requiring less data. For example, feature selection methods may be used to identify and remove unneeded, irrelevant and redundant attributes from data that do not contribute to the accuracy of the predictive model or may decrease the accuracy of the predictive model. An example of a predictive model is a neural network. According to an example embodiment of a neural network, the neural network includes an embedded filter layer that improves accuracy of the neural network.

Figure 1:
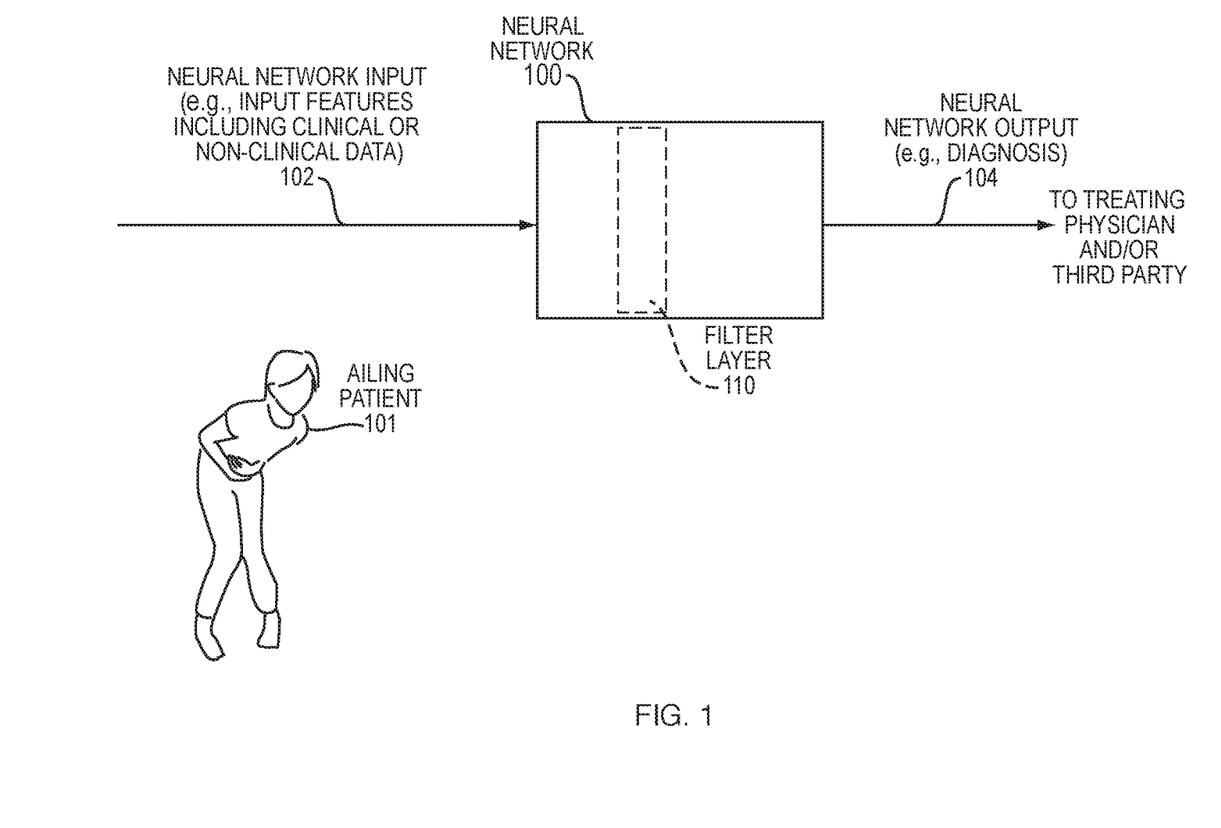
FIG. 1 is a block diagram of an example embodiment of an application of a neural network with a filter layer.

FIG. 1 is a block diagram of an example embodiment of an application of a neural network 100 with a filter layer 110. Dashed lines for the filter layer 110 indicate that the filter layer 110 can be located at various locations and may have various configurations within the neural network 100, as disclosed further below. The neural network 100 is configured to receive neural network input 102 and output neural network output 104. In the example embodiment, the neural network is trained to output a diagnosis, such as a clinical diagnosis, in response to receiving input features that may include clinical and non-clinical data. As such, the neural network input 102 may include input features, such as clinical and non-clinical data, and the neural network output 104 may include the diagnosis predicted based on same.

In the example embodiment, an amount of training data (not shown) may be low relative to a number of parameters (i.e., weights) that can be changed by the learning system (i.e., the neural network 100). Such a low amount of training data coupled with a large number of parameters may cause the neural network to generate associations that may not be meaningful. Such irrelevant associations may contribute to the neural network output 104, such as the diagnosis, absent the filter layer 110.

For example, an ailing patient 101 may be seen by a treating physician (not shown) for stomach pain. Clinical data, such as x-ray data, and non-clinical data, such as the treating physician, may be input features that are input to the neural network 100. Absent the filter layer 110, the neural network 100 may output a diagnosis, such as an ulcer, for the neural network output 104. Such a diagnosis may be output based on a learned association that corresponding to the treating physician. For example, the neural network 100 may learn an association between a diagnosis and the treating physician. Such a learned association may associate an ulcer diagnosis with the treating physician of the ailing patient 101 in an event the treating physician provides such a diagnosis frequently. By employing the filter layer 110, the neural network 100 may disregard such an association and provide the neural network output 104 with a different diagnosis, such as stomach cancer, that may be an accurate diagnosis for a condition of the ailing patient 101.

It should be understood that the neural network input 102 and the neural network output 104 and application of the neural network 100 disclosed above are for illustrative purposes and the neural network 100 with the filter 110 may be applied to any suitable application.

It should also be understood that the filter layer 110 may be embedded in any suitable neural network, such as a densely connected neural network, disclosed further below, convolutional neural network, recurrent neural network, or any other suitable network. Further, advantages, such as improved accuracy of the neural network 100, achieved by embedding the filter layer 110 therein, are not restricted to any particular ratio between an amount of data and parameters.

There are many strategies to achieve some amount of feature selection within a neural network. Most are strategies that try to detect and down-weigh less relevant input features. This is accomplished by decreasing the weights of outgoing connections connecting input features to the first hidden layer. In most architectures, this effectively "mutes" these features from the rest of the network beyond the first hidden layer. However, this does not apply as well to densely connected networks.

Densely connected networks are ones in which every node is connected to all nodes in all subsequent layers, and not only to nodes in the immediate next layer. Densely connected networks are not widely used but are gaining in popularity. In densely connected networks, input nodes connect to all other non-input nodes within the network. The "muting" effect cannot be accomplished since any node can assign any weight to the input feature. An example embodiment of the filter layer 110 enables such a "muting" effect to be accomplished in a densely connected network. Normal regularization in a densely connected neural network simply does not apply enough pressure on the outputs to assign weights of 0 to all of the outputs of a node. While an example embodiment of the filter layer 110 may be particularly suitable to a densely connected neural network, the filter layer 110 may be embedded in any suitable neural network, as disclosed above.

Figure 2:
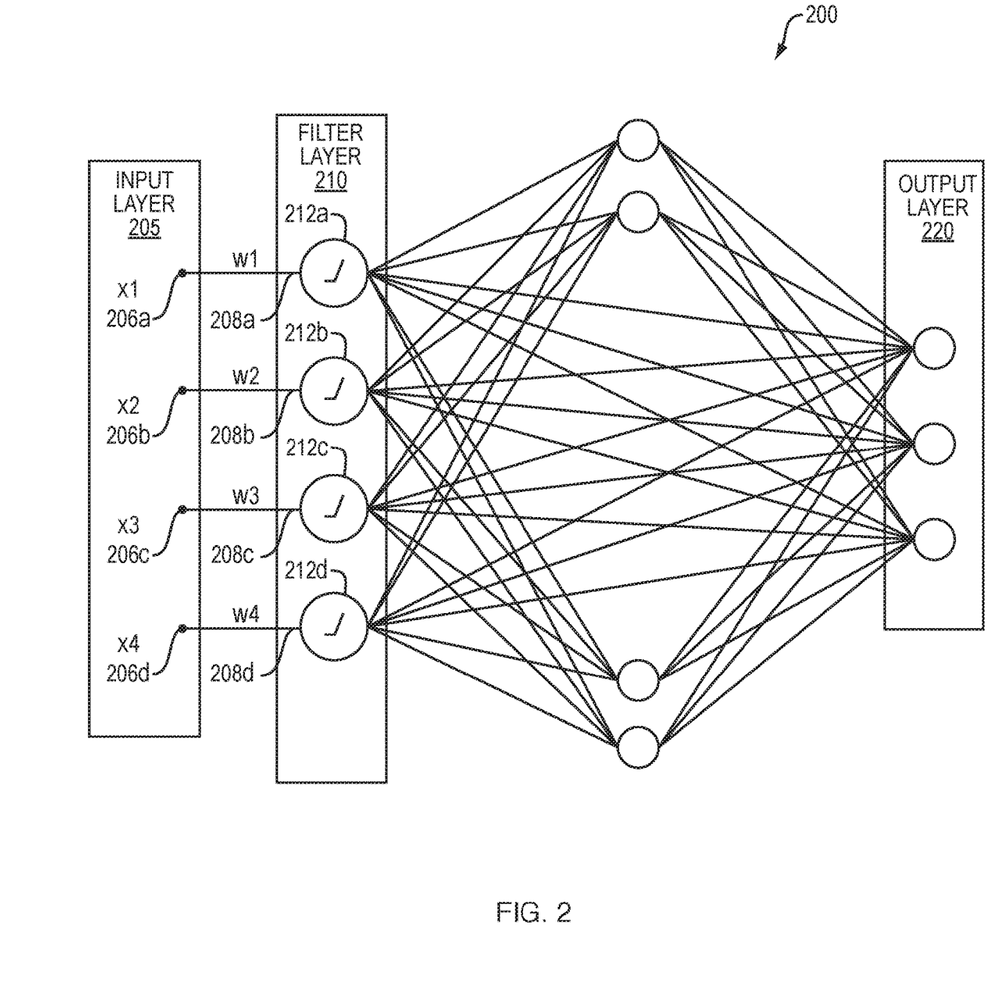
FIG. 2 is a network diagram of an example embodiment of a neural network with a filter layer.

FIG. 2 is a network diagram of an example embodiment of a neural network 200 with a filter layer 210. The neural network 200 comprises an input layer 205, output layer 220, and the filter layer 210. Each unit of the filter layer 210, namely, filter layer unit 212a, filter layer unit 212b, filter layer unit 212c, and filter layer unit 212d may be configured to receive a filter layer input from a single preceding unit via a respective filter layer input connection.

For example, the filter layer unit 212a receives the filter layer input x1 from a single preceding unit, that is, the input layer unit 206a, via the filter layer input connection 208a. The filter layer unit 212b receives the filter layer input x2 from a single preceding unit, that is, the input layer unit 206b, via the filter layer input connection 208b. The filter layer unit 212c receives the filter layer input x3 from a single preceding unit, that is, the input layer unit 206c, via the filter layer input connection 208c. The filter layer unit 212d receives the filter layer input x4 from a single preceding unit, that is, the input layer unit 206d, via the filter layer input connection 208d. As such, each of the filter layer input connections 208a-d is coupled to a different single preceding unit, namely, the input layer units 206a-d, respectively. It should be understood that since the preceding units 206a-d reside in the input layer 205, such units are passive and, thus, the input to such units, that is, x1-x4 passes through them unchanged and, thus, may be referred to as filter layer inputs in the example embodiment.

The filter layer 210 is configured to incentivize the neural network 200 to learn to produce a target output (not shown) from the output layer 220 for a given input (not shown) to the input layer 205 while simultaneously learning the weights w1, w2, w3, and w4, for each of the filter layer input connections 208a-d, respectively. The weights w1, w2, w3, and w4 are learned and cause the filter layer 210 to reduce a number of filter layer units that pass respective filter layer inputs as non-zero values. By reducing the number of filter layer units that pass respective filter layer inputs as non-zero values, information, such as irrelevant information, may be disregarded by the neural network 200 and its accuracy for prediction may be improved.

It should be understood that placement of the filter layer 210 within the neural network 200 is for illustrative purposes and that the filter layer 210 may be any suitable network layer between the input layer 205 and the output layer 220. According to an example embodiment the filter layer 210 may be a first filter layer and the neural network may further comprise at least one other filter layer (not shown).

According to an example embodiment, a filter layer may have input connections and output connections to respective units of internal layers that are neither input layers nor output layers. For example, as disclosed above, the filter layer may be embedded in a neural network in any suitable way and in any suitable type of neural network.

It should be understood that the term unit referred to herein may be referred to interchangeably as a node. A node, in the context of this disclosure, refers to a node of a layer as opposed to the layer itself. A number of nodes of the network 200 and within each of the input layer 205, filter layer 210, and output layer 220, are for illustrative purposes, and may be any suitable number.

According to an example embodiment, the filter layer may be inserted as a separate layer right after the input layer of a densely connected neural network. The only role of the filter layer may be to perform feature selection or filtering. As such, it is a one-to-one connected layer. A filter layer that is inserted right after the input layer of a neural network may be referred to interchangeably herein as a Feature Selection (FS) layer. Unlike other feature selection methods that down-weigh features, the FS layer blocks certain features by outputting solid zeros from the FS layer for input features that are rejected or cut. The filter layer that is not inserted right after the input layer may be referred to herein as simply, a filter layer.

It should be understood that a filter layer and an FS layer do not differ in function and that by referencing the filter layer as an FS layer simply indicates a location for the filter layer, that is, immediately following an input layer of the neural network. Further, filtering as performed by an FS layer may be referred to herein as feature selection as the FS layer is located such that input features are received at the FS layer as opposed to information from a preceding layer that is not an input layer.

To achieve this feature selection or filtering within the training process, a loss function of a filter layer and FS layer may be manipulated to push the network towards cutting some features or information. Given input features or filter layer input that is strictly positive, an example embodiment may achieve feature selection by using ReLU activations on the filter layer or FS layer's nodes and a special regularization function. Strictly positive input may be created at any point/location in a neural network by applying a sigmoid function to an input.

Figure 3:
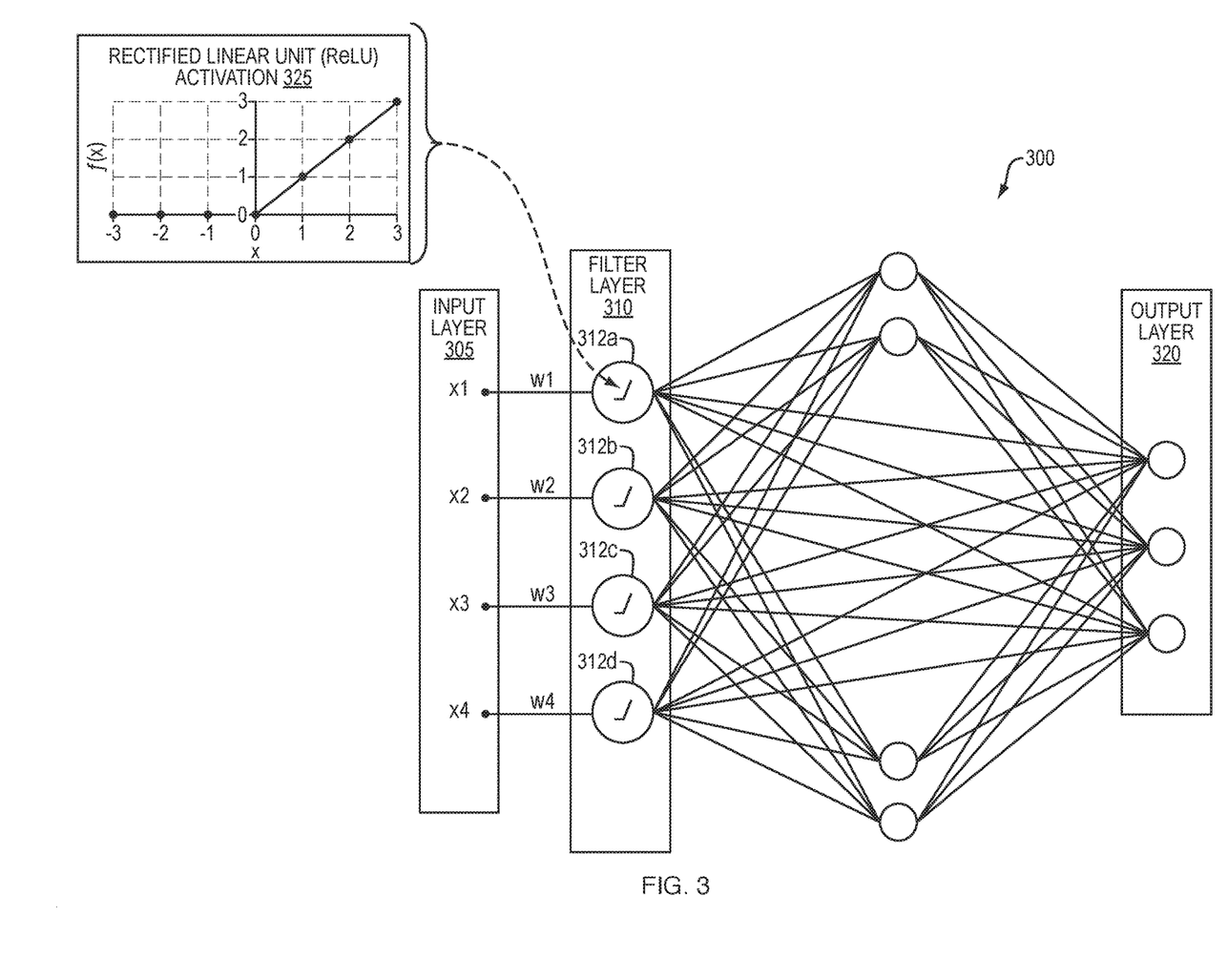
FIG. 3 is a network diagram of an example embodiment of a neural network with a filter layer wherein each unit of the filter layer is configured to apply a rectified linear unit (ReLU) activation function.

FIG. 3 is a network diagram of an example embodiment of a neural network 300 with a filter layer 310 wherein each unit of the filter layer 310 is configured to apply a rectified linear unit (ReLU) activation function 325. The neural network 300 comprises an input layer 305, output layer 320, and the filter layer 310. Each unit of the filter layer 310, that is, filter layer unit 312a, filter layer unit 312b, filter layer unit 312c, and filter layer unit 312d is configured to apply the ReLU activation function 325. The ReLU activation function 325 is defined as: $f(x)=\max(0, x)$.

Thus, the ReLU activation function 325 does not allow negative values through, instead replacing them with zeros. As such, since each unit of the filter layer 310 is configured to apply the ReLU activation function 325, each is configured to force all outputs from the filter layer unit to zero in an event a weight learned for its respective filter layer input connection is negative. According to an example embodiment, at least one of the weights w1, w2, w3, and w4 learned may have a negative value. Further, a mean of the weights learned may be a given average value.

According to an example embodiment, a filter layer, such as the filter layers 110, 210, and 310, disclosed above with reference to FIG. 1, FIG. 2, and FIG. 3, respectively, and the filter layer 410 of FIG. 4, disclosed further below, may be further configured to incentive the neural network to minimize a regularized loss function that is expressed on the filter layer that combines an underlying loss function with a penalty function imposed on the weights learned.

The regularized loss function may be deemed minimized in an event (i) a difference between an actual output from the output layer and the target output is less than or equal to a given acceptable difference and (ii) the weights learned have an average value that matches a given value causing the penalty function to achieve its minimum.

In theory, the underlying loss function may be minimized when the actual output from the output layer is substantially identical to the target output. As such, selection of a value of the given acceptable difference may be close to zero or any other suitable value that is acceptable based on requirements of the neural network application.

Effectively, a loss function expressed on the filter layer (and FS layer) may look like a standard regularized loss function:

$$L = V(f(X), Y) + P(w)$$

A learning process of the neural network may be configured to try to minimize the regularized loss function L disclosed above, in which:

Y is the target (i.e., desired) output.

$f(X)$ is the output of the network. The weights w are a component of $f$; that is, they are inside it. According to an example embodiment, a learn process of the neural network may be configured to learn $f$, and by extension, to learn w.

$V(f(X), Y)$ is the underlying loss function. It is at its minimum (normally zero) when $f(X)=Y$. In other terms, the minimum is achieved when actual output is as close as possible to target (i.e., desired) output.

L is a regularized version of $V(f(X), Y)$. It may be regularized by an example embodiment of an extra penalty term P(w). P(w) is a penalty or a constraint imposed on the choice of weights and, thus, could also be written as P($f$) as it is a penalty on the choice of the function $f$. According to an example embodiment, the penalty P is a penalty on the choice of weights because that is the part of $f$ selected to be constrained.

As such, the learning process may be trying to find an $f$ that comes as close as possible to $f(X)=Y$ while satisfying a constraint on $f$ by minimizing a penalty P($f$). According to the example embodiment, the penalty P is only on w, and, thus, the learning process is trying to find an $f$ that comes as close as possible to $f(X)=Y$ while satisfying the constraint on w by minimizing a penalty P(w).

For the regularization part, an example embodiment may use the following penalty:

$$P(w) = k\left(\frac{1}{N}\sum_{i=1}^{N}|w_i|\right) + l\left|\frac{1}{N}\sum_{i=1}^{N} w_i + s\right|$$

with tuning parameters k, l, and s. The penalty used can be interpreted as such:

The first term tuned by k is quasi-identical to an L1 regularization. The only difference is that it is normalized by N. The primary purpose of this L1 regularization term is to make sure weights are not assigned extreme values only to circumvent the penalty of a target mean regularization term, that is, the second term in the summation above.

The target mean regularization term tuned by l effectively accomplishes the selection. A zero penalty is achieved when the average of the weights is −s. As such, the neural network would be pushed towards picking weights with a −s average. As such, the weights learned may have an average negative value that matches a given negative value (i.e., −s). Depending on the selected s, the neural network is pushed towards assigning negative weights to some of the features which effectively cuts them out since the ReLU will not allow them through.

The following table illustrates an improvement obtained by adding the filter layer as an FS layer of a neural network applied to a difficult machine learning problem. The results show an improvement in Precision, Recall, and, thus, F1 score. The results shown are merely an illustration that the FS layer provides an improvement; however, different machine learning problems may observe different outcomes.

| | True Positives | False Positives | False Negatives | Precision | Recall | F1 Score |
|---|---|---|---|---|---|---|
| Without FS layer | 171 | 196 | 1112 | 46.6% | 13.3% | 20.7% |
| With FS layer | 222 | 212 | 1061 | 51.2% | 17.3% | 25.9% |

As disclosed above, the filter layer may be embedded in a neural network in any suitable manner. A filter layer that is embedded immediately following an input layer, such as a first internal or first hidden layer following the input layer, may be referred to interchangeably herein as a feature selection layer.

Figure 4:
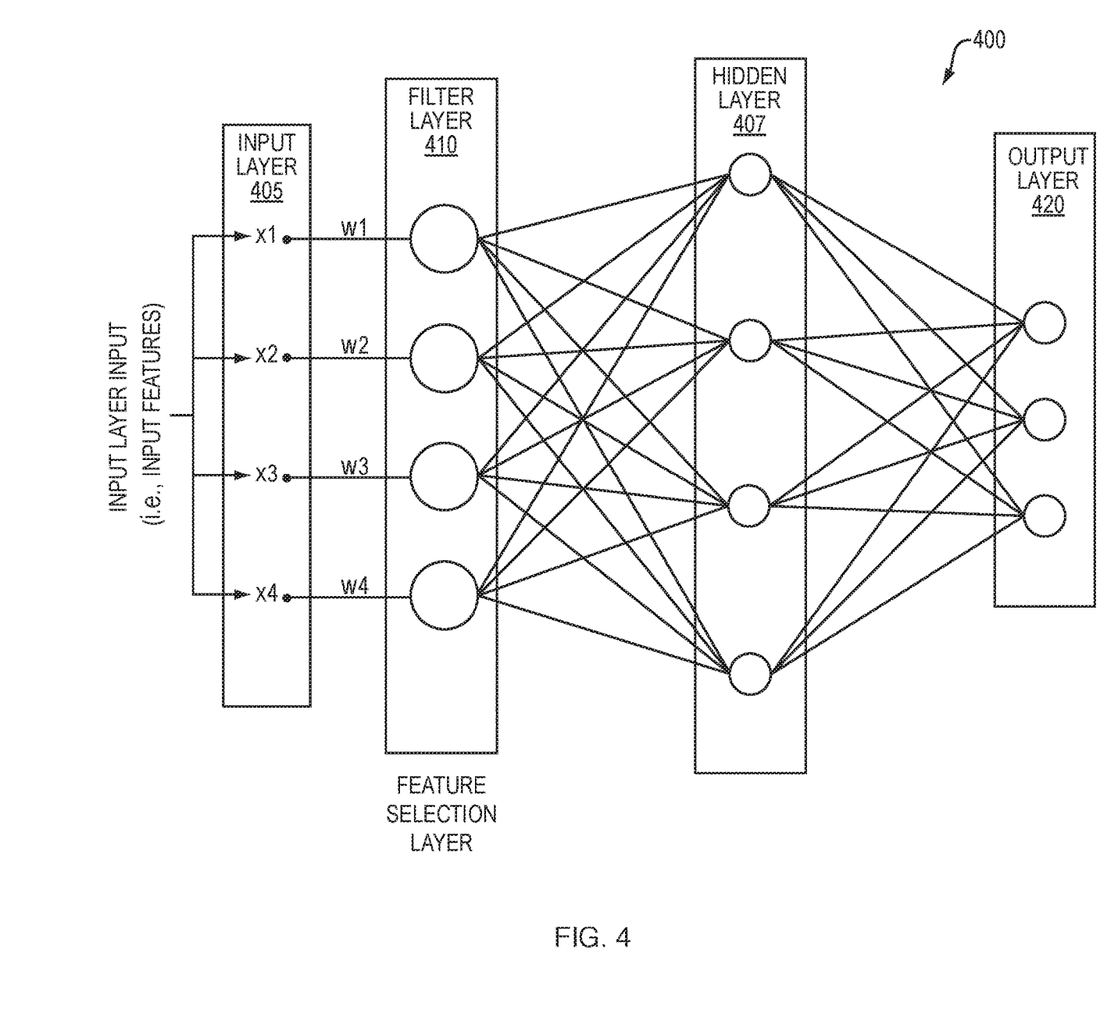
FIG. 4 is a network diagram of an example embodiment of a neural network with a filter layer that is a feature selection layer that is an initial hidden layer of the neural network.

FIG. 4 is a network diagram of an example embodiment of a neural network 400 with a filter layer 410 that is a feature selection layer that is an initial hidden layer of the neural network 400. As such, each filter layer input, namely, x1, x2, x3, and x4, in the example embodiment, is an input feature to the neural network 400. The neural network 400 comprises the input layer 405, output layer 420, and the filter layer 410. In addition, a hidden layer 407 is present; however, such a layer is for illustrative purposes and need not be present.

Figure 5:
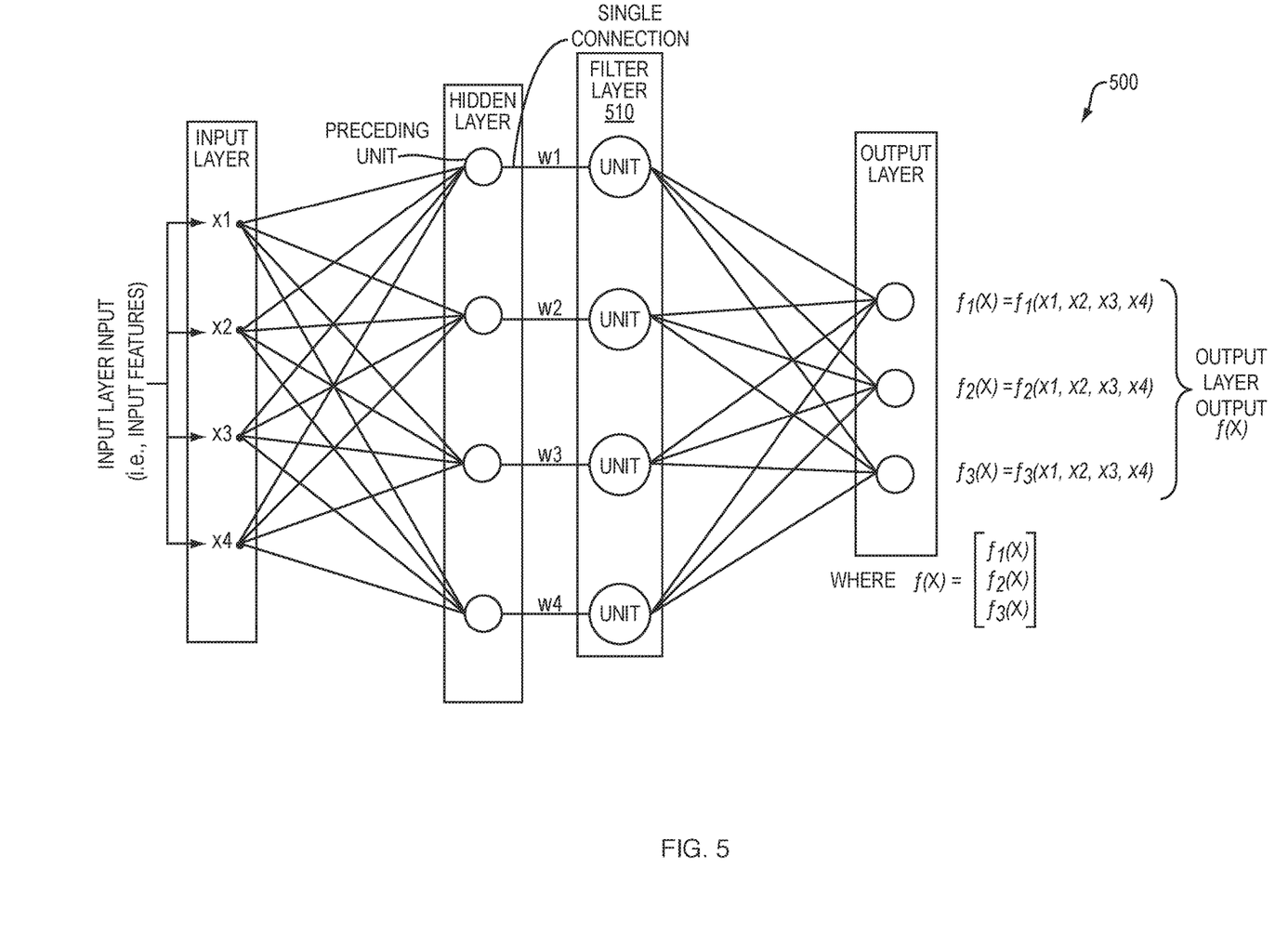
FIG. 5 is a network diagram of an example embodiment of a neural network with a filter layer that is a last hidden layer of the neural network.

FIG. 5 is a network diagram of an example embodiment of a neural network 500 with a filter layer 510 that is a last hidden layer of the neural network 500.

Figure 6:
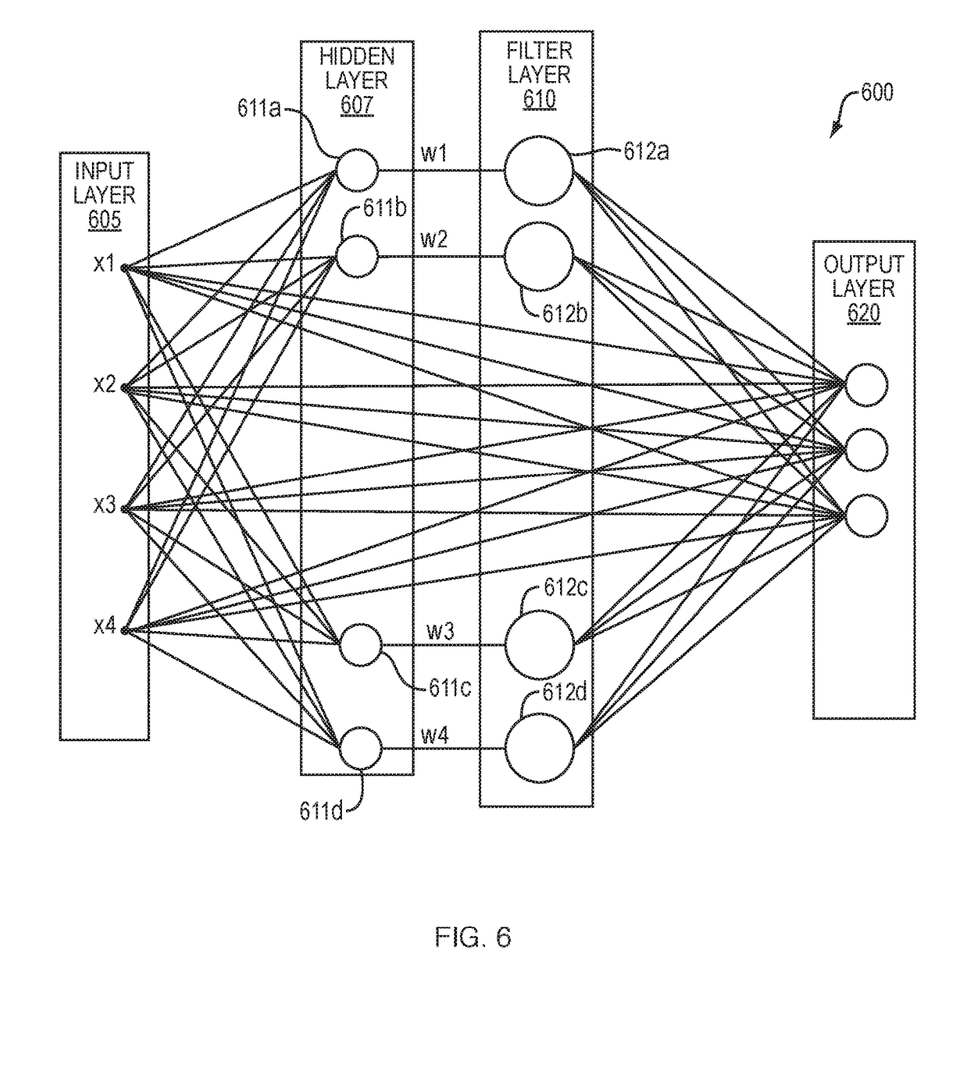
FIG. 6 is a network diagram of an example embodiment of a neural network with a filter layer having each unit of the filter layer configured to receive a filter layer input from a single preceding unit and each single preceding unit is located in a common preceding layer that precedes the filter layer.

FIG. 6 is a network diagram of an example embodiment of a neural network 600 with a filter layer 610 having each unit of the filter layer 610 configured to receive a filter layer input from a single preceding unit. Each single preceding unit is located in a common preceding layer that precedes the filter layer 610 in the neural network 600. For example, the neural network 600 comprises the input layer 605, output layer 620, filter layer 610, and the hidden layer 607. Each unit of the filter layer 610, namely filter layer unit 612a, 612b, 612c, and 612d, is configured to receive a filter layer input from a single preceding unit, namely 611a, 611,b, 611c, and 611d that are each located in a common preceding layer, that is, the hidden layer 607.

Figure 7:
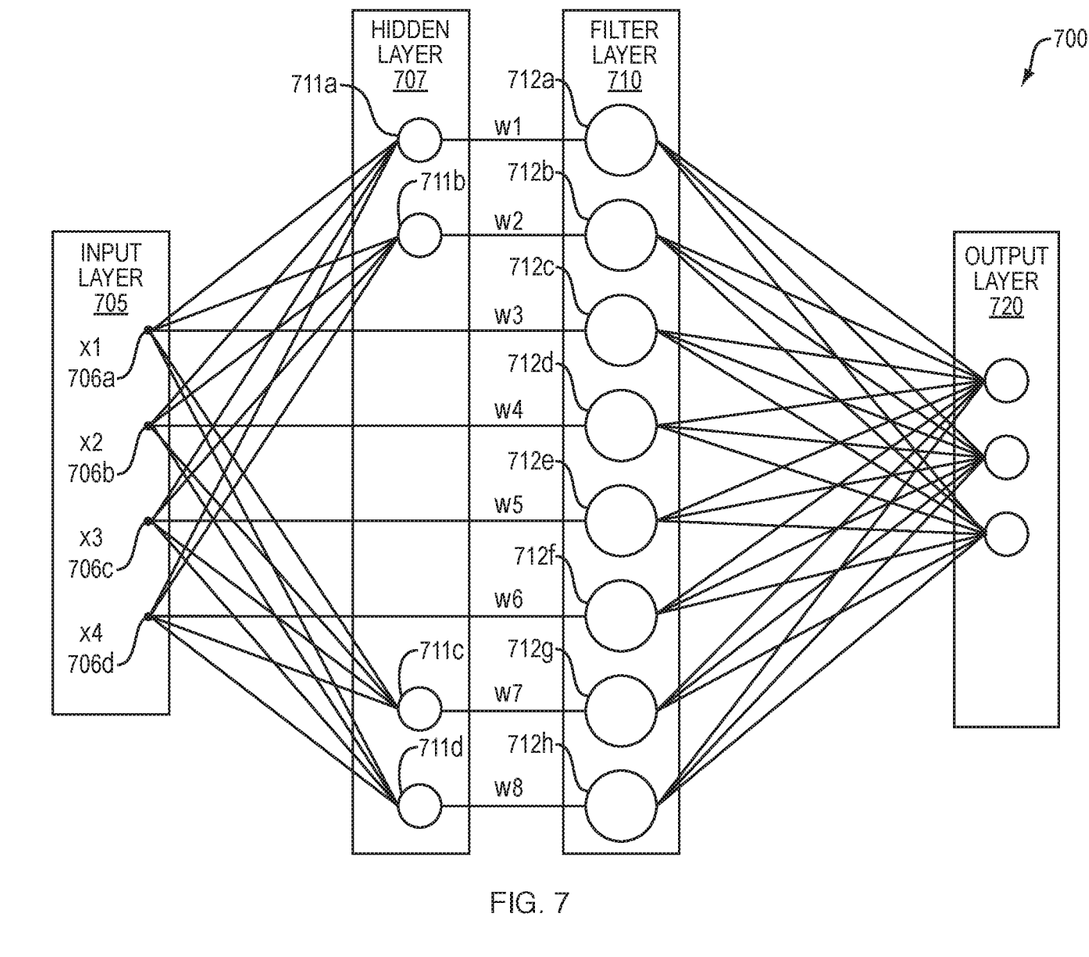
FIG. 7 is a network diagram of an example embodiment of a neural network with a filter layer having at least two units of the filter layer configured to receive respective filter layer inputs from corresponding single preceding units located in different preceding layers that precede the filter layer.

FIG. 7 is a network diagram of an example embodiment of a neural network 700 with a filter layer 710 having at least two units of the filter layer 710 configured to receive respective filter layer inputs from corresponding single preceding units located in different preceding layers that precede the filter layer 710 in the neural network 700.

For example, the neural network 700 comprises the input layer 705, output layer 720, filter layer 710, and the hidden layer 707. The input layer 705 includes the input layer units 706a-d and the hidden layer 707 includes the hidden layer units 711a-d. Each unit of the filter layer 710, namely filter layer unit 712a, 712b, 712c, 712d, 712e, 712f, 712g, and 712h is configured to receive a filter layer input from a single preceding unit, namely, the hidden layer unit 711a, hidden layer unit 711b, input layer unit 706a, input layer unit 706b, input layer unit 706d, input layer unit 706d, hidden layer unit 711c, and hidden layer unit 711d, respectively. As such, at least two units of the filter layer 710 are configured to receive respective filter layer inputs from corresponding single preceding units located in different preceding layers, namely, the input layer 705 and the hidden layer 707, that precede the filter layer 710 in the neural network 700.

Figure 8:
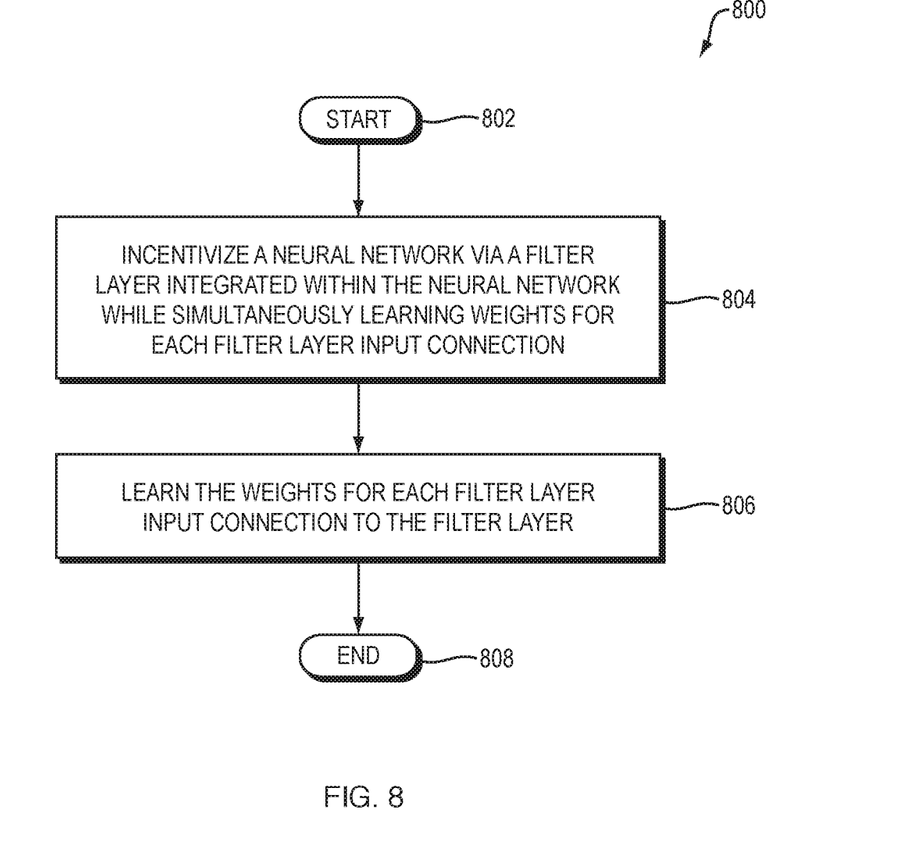
FIG. 8 is a flow diagram of an example embodiment of a method for filtering in a neural network.

FIG. 8 is a flow diagram 800 of an example embodiment of a method for filtering in a neural network. The method begins (802) and incentivizes the neural network, via a filter layer integrated within the neural network, to learn to produce a target output from an output layer for a given input to an input layer while simultaneously learning weights for each filter layer input connection, each unit of the filter layer configured to receive a filter layer input from a single preceding unit via a respective filter layer input connection, each filter layer input connection coupled to a different single preceding unit (804). The method learns the weights for each filter layer input connection to the filter layer, the weights learned causing the filter layer to reduce a number of filter layer units of the filter layer that pass respective filter layer inputs as non-zero values (806), and the method thereafter ends (808) in the example embodiment.

The method may further comprise applying a rectified linear unit (ReLU) activation function by each unit to force all outputs from the unit to zero in an event a weight learned for its respective filter layer input connection is negative, such as disclosed in FIG. 3, above. At least one of the weights learned may have a negative value and a mean of the weights learned may be a given average value. A non-positive (i.e., zero or negative) given average value, such as zero or a negative value, provides stricter filtering. A positive value provides less filtering and, possibly, no filtering.

The method may further comprise expressing a regularized loss function on the filter layer that combines an underlying loss function with a penalty function imposed on the weights learned, as disclosed above. Incentivizing the neural network may include incentivizing the neural network to minimize the regularized loss function as disclosed above. The method may further comprise deeming the regularized loss function to be minimized in an event (i) a difference between an actual output from the output layer and the target output is less than or equal to a given acceptable difference and (ii) the weights learned have an average value that matches a given value causing the penalty function to achieve its minimum.

Figure 9:
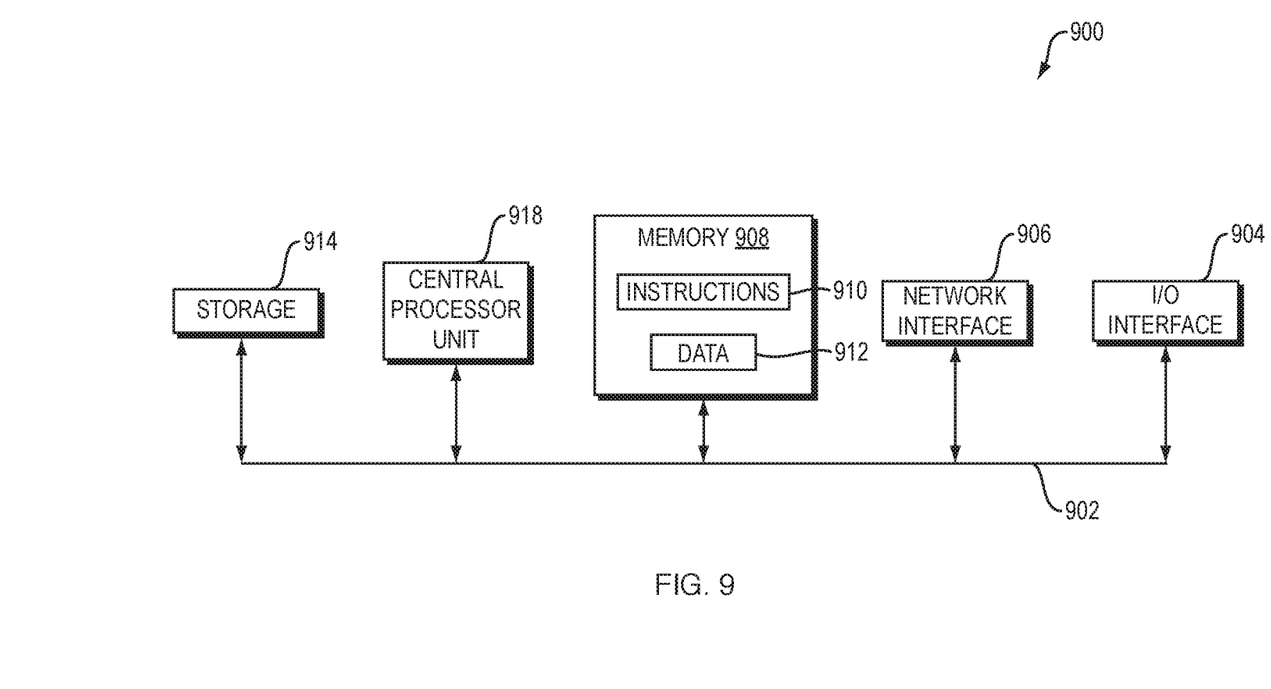
FIG. 9 is a block diagram of an example internal structure of a computer optionally within an embodiment disclosed herein.

The method may further comprise including each single preceding unit in a common preceding layer that precedes the filter layer in the neural network, as disclosed above with reference to FIG. 6, or configuring at least two units of the filter layer to receive respective filter layer inputs from corresponding single preceding units included in different preceding layers that precede the filter layer in the neural network, as disclosed above with reference to FIG. 7. When applied as an initial internal layer between an input layer and an output layer, the filter layer incentivizes the neural network to learn which neural network input features to discard to produce the target output FIG. 9 is a block diagram of an example of the internal structure of a computer 900 in which various embodiments of the present disclosure may be implemented. The computer 900 contains a system bus 902, where a bus is a set of hardware lines used for data transfer among the components of a computer or processing system. The system bus 902 is essentially a shared conduit that connects different elements of a computer system (e.g., processor, disk storage, memory, input/output ports, network ports, etc.) that enables the transfer of information between the elements. Coupled to the system bus 902 is an I/O device interface 904 for connecting various input and output devices (e.g., keyboard, mouse, displays, printers, speakers, etc.) to the computer 900. A network interface 906 allows the computer 900 to connect to various other devices attached to a network. Memory 908 provides volatile or non-volatile storage for computer software instructions 910 and data 912 that may be used to implement embodiments of the present disclosure, where the volatile and non-volatile memories are examples of non-transitory media. Disk storage 914 provides non-volatile storage for computer software instructions 910 and data 912 that may be used to implement embodiments of the present disclosure. A central processor unit 918 is also coupled to the system bus 902 and provides for the execution of computer instructions.

Further example embodiments disclosed herein may be configured using a computer program product; for example, controls may be programmed in software for implementing example embodiments. Further example embodiments may include a non-transitory computer-readable medium containing instructions that may be executed by a processor, and, when loaded and executed, cause the processor to complete methods described herein. It should be understood that elements of the block and flow diagrams may be implemented in software or hardware, such as via one or more arrangements of circuitry of FIG. 6, disclosed above, or equivalents thereof, firmware, a combination thereof, or other similar implementation determined in the future. In addition, the elements of the block and flow diagrams described herein may be combined or divided in any manner in software, hardware, or firmware. If implemented in software, the software may be written in any language that can support the example embodiments disclosed herein. The software may be stored in any form of computer readable medium, such as random access memory (RAM), read only memory (ROM), compact disk read-only memory (CD-ROM), and so forth. In operation, a general purpose or application-specific processor or processing core loads and executes software in a manner well understood in the art. It should be understood further that the block and flow diagrams may include more or fewer elements, be arranged or oriented differently, or be represented differently. It should be understood that implementation may dictate the block, flow, and/or network diagrams and the number of block and flow diagrams illustrating the execution of embodiments disclosed herein.

While example embodiments have been particularly shown and described, it will be understood by those skilled in the art that various changes in form and details may be made therein without departing from the scope of the embodiments encompassed by the appended claims.

What is claimed is:

1. A neural network, comprising;
   an input layer;
   an output layer; and
   a filter layer, each unit thereof configured to receive no more than a single filter layer input, the single filter layer input being a filter layer input received from a single preceding unit via a respective filter layer input connection, each filter layer input connection coupled to a different single preceding unit, the filter layer configured to incentivize the neural network to learn to produce a target output from the output layer for a given input to the input layer while simultaneously learning weights for each filter layer input connection, the weights learned causing the filter layer to reduce a number of filter layer units that pass respective filter layer inputs as non-zero values, the weights learned having an average negative value that matches a given negative value, wherein the given negative value is a selected value for a tuning parameter of the neural network, the selected value causing the neural network to assign negative weights to at least a portion of the weights learned, and wherein each unit of the filter layer is configured to apply a rectified linear unit (ReLU) activation function to force all outputs from the unit to zero in an event a weight learned for its respective filter layer input connection is negative.

2. The neural network of claim 1, wherein the filter layer is further configured to incentivize the neural network to minimize a regularized loss function that is expressed on the filter layer that combines an underlying loss function with a penalty function imposed on the weights learned.

3. The neural network of claim 2, wherein the regularized loss function is deemed minimized in an event (i) a difference between an actual output from the output layer and the target output is less than or equal to a given difference and (ii) the weights learned have the average negative value that matches the given negative value causing the penalty function to achieve the penalty function's minimum.

4. The neural network of claim 1, wherein the filter layer is a feature selection layer that is an initial hidden layer of the neural network and each filter layer input is an input feature to the neural network.

5. The neural network of claim 1, wherein the filter layer is a last hidden layer of the neural network.

6. The neural network of claim 1, wherein the filter layer has input connections and output connections to respective units of internal layers that are neither input layers nor output layers.

7. The neural network of claim 1, wherein each single preceding unit is located in a common preceding layer that precedes the filter layer in the neural network.

8. The neural network of claim 1, wherein at least two units of the filter layer are configured to receive respective filter layer inputs from corresponding single preceding units located in different preceding layers that precede the filter layer in the neural network.

9. The neural network of claim 1, wherein the filter layer is a first filter layer and the neural network further comprises at least one other filter layer.

10. The neural network of claim 1, wherein the neural network is a densely connected neural network that includes the filter layer integrated therein.

11. A method for filtering in a neural network, the method comprising:

incentivizing the neural network, via a filter layer integrated within the neural network, to learn to produce a target output from an output layer for a given input to an input layer while simultaneously learning weights for each filter layer input connection, each unit of the filter layer configured to receive no more than a single filter layer input, the single filter layer input being a filter layer input received from a single preceding unit via a respective filter layer input connection, each filter layer input connection coupled to a different single preceding unit;

learning the weights for each filter layer input connection to the filter layer, the weights learned causing the filter layer to reduce a number of filter layer units of the filter layer that pass respective filter layer inputs as non-zero values, the weights earned having an average negative value that matches a given negative value; and applying a rectified linear unit (ReLU) activation function by each unit to force all outputs from the unit to zero in an event a weight learned for its respective filter layer input connection is negative, wherein the given negative value is a selected value for a tuning parameter of the neural network, the selected value causing the neural network to assign negative weights to at least a portion of the weights learned.

12. The method of claim 11, further comprising expressing a regularized loss function on the filter layer that combines an underlying loss function with a penalty function imposed on the weights learned, wherein incentivizing the neural network includes incentivizing the neural network to minimize the regularized loss function.

13. The method of claim 12, further comprising deeming the regularized loss function to be minimized in an event (i) a difference between an actual output from the output layer and the target output is less than or equal to a given difference and (ii) the weights learned have the average negative value that matches the given negative value causing the penalty function to achieve the penalty function's minimum.

14. The method of claim 11, wherein the filter layer is a feature selection layer that is an initial hidden layer of the neural network and each filter layer input is an input feature to the neural network.

15. The method of claim 11, wherein the filter layer is a last hidden layer of the neural network or wherein the filter layer has input connections and output connections to respective units of internal layers that are neither input layers nor output layers.

16. The method of claim 11, further comprising including each single preceding unit in a common preceding layer that precedes the filter layer in the neural network or configuring at least two units of the filter layer to receive respective filter layer inputs from corresponding single preceding units included in different preceding layers that precede the filter layer in the neural network.

17. The method of claim 11, wherein the filter layer is a first filter layer and the method further comprises including at least one other filter layer in the neural network.

18. The method of claim 11, wherein the neural network is a densely connected neural network that includes the filter layer integrated therein.

* * * * *

UNITED STATES PATENT AND TRADEMARK OFFICE
CERTIFICATE OF CORRECTION

PATENT NO. : 11,256,973 B2
APPLICATION NO. : 15/888812
DATED : February 22, 2022
INVENTOR(S) : Nasr Madi and Neil D. Barrett It is certified that error appears in the above-identified patent and that said Letters Patent is hereby corrected as shown below:

In the Claims

In Claim 11, Column 12, Line 5, please delete "earned" and insert --learned--.

Signed and Sealed this
Twenty-sixth Day of April, 2022

Katherine Kelly Vidal
*Director of the United States Patent and Trademark Office*